United States Patent [19]

Melnick et al.

[11] 4,145,304

[45] Mar. 20, 1979

[54] RESIN AND METHOD FOR REMOVING ANTIMICROBIALS FROM BODY FLUIDS

[76] Inventors: Joseph L. Melnick, 8838 Chatsworth Dr.; Craig Wallis, 11002 Hedwig Green, both of Houston, Tex. 77024

[21] Appl. No.: 856,851

[22] Filed: Dec. 2, 1977

[51] Int. Cl.$^2$ .......................... B01J 1/04; B01D 15/04; G01N 31/04; G01N 33/16
[52] U.S. Cl. ...................... 252/182; 422/44; 422/101; 210/36; 252/184; 424/79; 424/DIG. 7; 195/1.8
[58] Field of Search ................. 252/182, 184; 210/36; 23/230 B, 258.5 B; 424/31, 79, DIG. 7

[56] References Cited

U.S. PATENT DOCUMENTS

| | | | |
|---|---|---|---|
| 2,689,227 | 9/1954 | McBurney | 210/37 R |
| 2,987,441 | 6/1961 | Brudney | 424/79 |
| 3,620,681 | 11/1971 | Wright | 23/258.5 R |
| 3,625,652 | 12/1971 | Fujimoto et al. | 23/230 B |
| 3,753,655 | 8/1973 | Schreiber et al. | 23/230 B |
| 3,794,584 | 2/1974 | Kunis | 424/79 |
| 3,856,471 | 12/1974 | Winitz et al. | 23/230 B |

*Primary Examiner*—Benjamin R. Padgett
*Assistant Examiner*—Irwin Gluck

[57] ABSTRACT

Microporous anionic exchange and non-ionic adsorbent resins which are capable of adsorbing an antibiotic and which have been coated with a non-ionic detergent are disclosed. When contacted with bacterially infected body-fluid specimens, the disclosed resins remove antibiotics from the specimen while exhibiting diminished bacterial adsorption. A combination of a disclosed detergent-coated non-functional adsorbent resin with a cationic resin removes other bacterial inhibitors, as well as antibiotics, from bacterially infected body fluid specimens while permitting the bacteria to remain in the specimens. By removing bacterial inhibitors while sparing the bacteria, the disclosed resins make possible rapid isolation and identification of an infecting organism.

11 Claims, No Drawings

RESIN AND METHOD FOR REMOVING ANTIMICROBIALS FROM BODY FLUIDS

BACKGROUND OF THE INVENTION

Despite the availability of excellent antimicrobial drugs, the mortality from bacteremia remains high, especially when shock accompanies sepsis. Early administration of an appropriate antibiotic greatly improves the chances for survival of a patient suffering from bacteremia. It is thus imperative that the identification and susceptibility of the infecting organism be determined as early as possible in the course of bacteremia.

When conventional techniques are employed to identify an infecting organism, however, several days to as long as two weeks may be required for adequate growth and isolation of an organism contained in blood. This may be due to the administration of an antibiotic prior to drawing the blood sample for testing. The presence of the antibiotic in the blood can result in inhibition of the growth of bacteria, thus interfering with isolation and identification of the offending bacterium.

Bacteremia is associated with nosocomial procedures, being related to use of urinary catheters, respiratory and intravenous therapy and hyperalimentation. In these cases and others, where antibiotics may not be present in the blood, the isolation of the offending organisms still may require excess periods of incubation because of inhibitors contained in serum, plasma or lysed erythrocytes.

Bacteriuria is also difficult to establish when the patient has been placed on antibiotics and is excreting antibiotics in the urine along with the bacteria. Direct plating of urine for isolation of bacteria in such cases in usually ineffective since the inoculum also contains the antibiotic. Thus, culturing for the causative agent is often difficult due to the presence of antimicrobial agents.

Similar problems exist when other body fluids, such as spinal fluid, abscess exudates, and the like, are examined.

The present conventional method for detection of bacteria or fungi in cases of septicemia or for detection of bacteriuria or bacterial meningitis is to inoculate 5 ml of whole blood, urine or spinal fluid into a culture medium and wait for the appearance of turbidity, which manifests bacterial growth. Patients who have been on antibiotic therapy will have the antibiotic in their blood, urine or spinal fluid at the time the culture is initiated. The presence of the antibiotic will inhibit growth of the bacteria and may delay isolation of the offending organism for as long as 14 days and sometimes longer.

More rapid detection of bacteria in blood is presently possible by employing radioactive $CO_2$ in the culture. Since bacteria metabolize $CO_2$, the disappearance of the tagged carbon dioxide indicates the presence of bacteria. Although this method may rapidly determine the presence of bacteria in blood cultures in the absence of antibiotics or other inhibitors, it is inefficient when bacteriostasis occurs due to the presence of antibiotics or other inhibitors in the blood cultures.

Recent methods for the separation of antibiotics from bacteria by membrane chromatography have been reported, but these procedures are not presently practical because of the manipulations required and the high rate of contamination of the test cultures by exogenous organisms. Thus, rapid isolation and identification of bacteria in body fluid specimens is not possible using conventional methods where the specimen contains bacterial inhibitors.

Although resin exchangers and adsorbents are known to adsorb charged antibiotics from fluid specimens, they have not proven to be a satisfactory means for removing antibiotics from bacterially infected specimens where rapid isolation and identification of an infecting bacterium is the objective. The reason for this is that upon passage of a specimen containing an anionic antibiotic and an infecting organism through an anionic exchange resin, the resultant filtrate is not only substantially freed of the antibiotic, but the infecting bacteria are also significantly removed by the resin exchanger.

It is therefore an object of the present invention to provide a means for the rapid isolation and identification of an infecting organism in a body fluid specimen.

It is another object of this invention to provide a means for selectively removing bacterial inhibitors from body fluid specimens.

It is a further object of the present invention to provide a means for removing antibiotics from a bacterially infected body fluid specimen without significantly reducing the bacterial count of the specimen.

It is yet another object of the present invention to provide a resin which will adsorb charged antibiotics contained in a body fluid specimen while exhibiting diminished adsorption of bacteria from the specimen.

It is still another object of the present invention to provide a resin for removing materials inhibitory to bacteria from body fluid specimens while sparing a significant number of bacteria.

SUMMARY OF THE INVENTION

This invention relates to microporous ion exchange and adsorbent resins and their use in the selective removal of charged antibiotics and other bacterial inhibitors from bacterially infected body fluid specimens. The resins of the invention are microporous ion exchange and adsorbent resins, characterized by a capacity for adsorption of antibiotics, which have been coated with a non-ionic detergent, particularly the detergent sold under the trademark Triton X-100.

When a biological fluid specimen containing bacteria and a charged antibiotic is contacted with such a resin, the antibiotic is adsorbed and the number of viable bacteria which efficiently pass the resin do not adhere to or become adsorbed on the resin is increased. A combination of such a detergent-treated non-functional polymeric adsorbent resin with a cationic resin selectively removes other bacterial inhibitors as well as antibiotics from bacterially infected body fluid specimens. Thus, the detergent-coated resins of the invention provide a means for selectively removing charged antibiotics and other antimicrobials from body fluid specimens while leaving a significant number of the bacteria substantially intact in the filtrate. Rapid culturing and analysis of the bacteria in the specimen are thereby made possible.

DETAILED DESCRIPTION OF THE INVENTION

In accordance with the present invention, a microporous resin capable of adsorbing an antibiotic is coated with a non-ionic detergent. The resin so provided selectively adsorbs the antibiotic from body fluid specimens, such as blood or urine, while sparing bacteria contained in such specimens.

The resins which may be employed in the present invention are microporous resins or combinations of resins which are known to adsorb charged antibiotics. These microporous resins are coated with a non-ionic detergent to form the resins of the invention by fluidizing the resins with the detergent. When biological fluid specimens containing anionic or cationic antibiotics and bacteria are contacted with the appropriate resins of the invention, the antibiotic is adsorbed on the resin and the bacteria remains in the filtrate. The pathogen-containing filtrate can then readily be cultured and/or analyzed according to conventional techniques.

Similarly, when a bacterially infected body fluid specimen containing bacterial inhibitors besides antibiotics is contacted with a detergent-coated non-functional polymeric adsorbent resin in combination with a cationic resin, the bacterial inhibitors as well as antibiotics are adsorbed while a significant number of bacteria are spared. Thus, the resins and the method of this invention selectively remove antibiotics and other antimicrobials which normally retard and even prevent growth of bacteria in body fluid specimens contaminated with such inhibitors, thereby permitting rapid identification and determination of the susceptibility of an infecting organism.

It is to be understood that throughout this application, the selective adsorption by the resins of the invention refers to the ability of the resins to adsorb bacterial inhibitors while exhibiting diminished bacterial adsorption. Such references are without regard to the resins' effect on materials which may be present in the specimen in addition to the bacteria and bacterial inhibitors.

More particularly, the resins which may be used to practice this invention are anionic and cationic resin exchangers and non-functional polymeric resin adsorbents which can effectively completely remove anionic and cationic antibiotics from body fluid specimens and will not completely adsorb bacteria when treated with a detergent in accordance with the invention. The degree of removal of a material by a resin is, of course, dependent on factors, such as the total exchange capacity, pore diameter and surface area of the resin. Thus, these factors must be considered in selecting an appropriate resin for use in the invention.

The resins which may be employed in the practice of the invention include synthetic ion exchange resins and non-functional adsorbent resins with matrices formed from condensation and addition polymers. Specifically, polystyrene resins cross-linked with divinyl benzene may be employed. The resin employed in the invention may be in the form of granules or spherical beads.

Generally, resins do not have a pore size sufficient to permit bacteria to penetrate into the interior of the resin. However, certain resins have macroporous structures with large internal surfaces which permit large molecules to penetrate their interiors. Such macroporous resins should be avoided in the practice of this invention since bacteria appear to become entrapped within such resins. Resins which have relatively smaller pores with adsorption being effected principally on the external surfaces of the resins, that is, microporous resins, are therefore recommended in contradistinction to macroporous resins. For purposes of this application, the term microporous is intended to signify such sub-macroporous resins.

The microporous ion exchange resins which may be used may either be strong or weak base anion exchange resins having quaternary ammonium or polyalkyl amine functional groups. In such anionic resins, the mobile ion may be any anionic group which exchanges with an antibiotic. Chloride charged anion exchange resins have generally been found to be suitable.

Specifically, the chloride charged anionic exchange resins and the adsorbent resin sold under the following trademarks have been found effective in the practice of the invention when treated with non-ionic detergents: Dowex 1-X8 from Dow Chemical Company, Duolite A-109 from Diamond Shamrock Company and Amberlite IRA 400 from Rohm & Haas, all of which are strong base resins having polystyrene quaternary ammonium functional groups; Duolite A-7 from Diamond Shamrock Company and Amberlite IR 45 from Rohm & Haas, which are weakly basic and have tertiary amine functional groups; and XAD-4 from Rohm & Haas, which is a non-functional copolymer of styrene and divinyl benzene, and has a macroreticular structure with 20–50 mesh, a density of 1.20 g/ml and a pore diameter of 80 Å.

In accordance with the invention, the microporous resins are coated with detergents which diminish bacterial adsorption by a resin. The detergents which have been found effective in the practice of the invention are non-ionic detergents. Cationic detergents generally cannot be used because of their disinfectant properties. In addition, it has been found that at least some anionic detergents cause even further reduction in bacterial count than is observed when resins which had been treated with no detergent are employed. This reduction in bacterial count was observed, for example, when a sample containing *Staphylococcus aureus* was eluted through an XAD-4 resin treated with the anionic detergent, sodium lauryl sulfate.

Preferred non-ionic detergents for use in the practice of the invention are the polyethylene glycol alkyl aryl ether detergents. Specifically, the detergent of this type sold under the trademark Triton X-100 has been found particularly effective in the practice of the invention. Non-ionic sorbitan monocarboxylate polyoxyalkylene detergents, specifically those sold under the trademarks Tween 20 (sorbitan monolaurate polyoxyalkylene), 40 (sorbitan monopalmitate polyoxyalkylene), 60 (sorbitan monostearate polyoxyalkylene) and 80 (sorbitan monooleate polyoxyalkylene), though operative, do not prevent bacterial adsorption to the same degree as Triton X-100. In most instances, the Tweens reduce bacterial adsorption on an XAD-4 adsorbent by 3–5%.

The resins of the invention are coated with a detergent by fluidizing the resins with a non-ionic detergent and thereafter removing detergent in excess of that coating the resins. The nature of the chemical and physical interaction of the detergent and resin made in accordance with this invention is not fully understood. It is believed, however, that the detergent is in the nature of a spatial coating on the resin.

The treatment by which resins may be coated with a non-ionic detergent to construct the resins of the invention may be effected by percolating a sample of detergent dissolved in sterile distilled water through a resin column until the column is fluidized with the detergent. Thus, the effluent is discarded until the detergent is contained within the resin bed, and not above the bed. Excess detergent present in the resin after a resin has been fluidized may be removed by aspirating the fluid phase of the resin bed after the detergent and resin have been in contact with one another for some 15 min or more. An appropriate amount of the resin so prepared may then be placed in a vial which can be sealed with an appropriate stopper and sterilized.

In accordance with this invention, an ion exchanger adsorbent resin treated with a detergent as above described is used to remove antibiotics from body fluid specimens by contacting the specimen with the treated resin. In instances where bacterial inhibitors other than antibiotics are present in a body fluid sample, a detergent-treated resin in accordance with this invention in combination with a cationic resin may be employed to remove such inhibitors from the specimen. A particularly preferred combination is a detergent-coated non-functional polymeric adsorbent resin, such as XAD-4, and a cationic exchange resin. Such a combination resin will adsorb antibiotics, as well as other bacterial inhibitors, while sparing a significant number of bacteria contained in a body fluid specimen.

Not all resins have the same capacity to adsorb an antibiotic. For example, the 1-X8, IRA 400, A-7, IR 45 and XAD-4 resins all efficiently remove 2 ug/ml penicillin G potassium from blood samples containing 5 ml of whole blood in 5 ml of water when contacted with 30 grams of resins treated with Triton X-100. However, the amount of resin was reduced to 12.5 grams, XAD-4 adsorbent was capable of removing 100% of the antibiotic, whereas the other resins failed to efficiently remove the penicillin in the blood with this amount of resin. Due to this greater efficiency, XAD-4 is a preferred resin for use in adsorbing anionic antibiotics in the practice of the invention.

The above-noted reduction in efficiency observed with anionic exchange resins is not observed with cationic exchange resins. Thus, when blood treated as described above was used as a diluent for gentamycin sulfate (2 ug/ml) instead of penicillin G potassium, all cationic resins tested efficiently removed the antibiotic even at levels of 1 gram of resin for every 10 ml blood-water mixture.

It is evident that in the case of anionic resins, the increased amount of resin required is due to the fact that blood serum and plasma have anionic components that compete with the antibiotic for the resin sites. Thus, the amount of anionic resin must be sufficient to provide the sites necessary to satisfy both the antibiotic and the competitive components in the blood. On the other hand, serum, plasma, blood, spinal fluid, and urine have few organic cationic components and thus the requirement for cationic resin is less. Therefore, although no more than 5 grams of cationic resin are generally required with a 5 ml sample of blood, 12.5 grams of even the more efficient XAD-4 adsorbent may be required to effect adequate adsorption of anionic materials.

The resins of the invention will selectively adsorb antibiotics and other bacterial inhibitors from bacterially infected body fluid specimens including urine, blood, spinal fluid and the like. Generally, with blood specimens, about 1:5 dilution of whole blood in saline may be passed through or otherwise contacted with a resin made in accordance with the invention. The filtrate thereof may then be mixed with culture broth to a final 1:10 dilution of the blood. The culture broth mixture obtained is then ready to be placed to test for bacterial activity.

In using the invention with blood specimens, the sample may be obtained conventionally by venous puncture with 5 ml of whole blood being obtained in a syringe. The blood sample may then be transferred aseptically to a vial containing the resins by perforating the stopper with the syringe needle and injecting the 5 ml of whole blood into the vial. The vial may be placed on a rotary shaker and shaken for 15 min at a speed which allows good collision efficiency between the resin and blood. In practice, it is recommended that a rotary shaker at 250–300 rpm be used.

Any other type of apparatus or method which effects sufficient contact between the resin and the specimen to assure adsorption of the antibiotic on the resin may also be employed. For example, it has been found highly effective to tumble a resin and specimen in a vertically rotating container. By slowly rotating such a container, a very high level of collision efficiency is achieved and a reduction in the potential for traumatic effects on the bacteria results. Such tumbling may be accomplished by attaching a closed vial containing the resins of the invention and the specimen to a revolving gear mechanism in a manner which results in end-over-end rotation of the vial.

After shaking, tumbling, or otherwise contacting a blood specimen with the resin, the sample may be withdrawn from the vial by inserting a needle through the stopper with at least 5 ml of the blood-water mixture being removed by negative pressure from the vial into a syringe. The sample may then be inoculated into blood culture broth using conventional techniques. Again employing conventional methods, the cultures are incubated, generally at 35–36° C., until turbidity is manifest in the culture. At that time, the sample is considered positive and the required measures can then be taken to treat the patient. When an antibiotic-containing specimen is contacted with a resin of the invention, the period of time required for turbidity to appear is substantially less than when such an antibiotic-containing specimen is not contacted with a resin of the invention.

Substantially the same procedures as described above are used when antibiotics are to be removed from spinal fluid, urine and other body fluids. On occasion, however, it may be difficult to obtain a 5 ml sample of spinal fluid. If 5 ml samples can be obtained, they should be used for the test. If not, any volume obtained will have to be injected into the resin vial and withdrawal of as much fluid as possible accomplished after the shaking time indicated. The resin eluates are inoculated into bacteriological media as described above.

In one specific embodiment of the invention, a combination of microporous non-ionic polymeric resin adsorbent coated with a non-ionic detergent in combination with a cationic resin is used to separate antibiotics and other bacterial inhibitors from bacterially infected body fluid samples. One particularly effective and highly preferred combination resin may be prepared as follows:

XAD-4 adsorbent: 100 grams of XAD-4 resin is placed in a column and washed with 200 ml of distilled water and then with 200 ml of 70% ethanol to remove contaminating compounds. The resin is then washed with 200 ml of distilled water to remove residual alcohol and then 200 ml of 0.1% Triton-100 is allowed to slowly percolate through the column. The resin column is cleared of excess detergent using positive air pressure.

C-249 cation exchanger (Ionac) or IRC 50 (Rohm and Haas): 40 grams of cation resin is placed in a column, and the column is treated with 200 ml of distilled water and then 200 ml of 70% ethanol and washed with 200 ml of distilled water to remove the residual ethanol. The resin is then charged with $Na^+$ by slowly passing 400 ml of 1 M NaCl through the column. The column is washed with 400 ml of distilled water to remove residual salt and is then air-dried with positive pressure.

100 grams of the XAD-4 adsorbent and 40 grams of the C-249 cation resin or other acceptable cation resin, prepared as above described, are combined in an appropriate vessel, such as a beaker, and 24 ml of distilled water are added to make a slurry. The slurry is mixed vigorously with a stirring device to suspend the resins. Then 20.5 ml aliquots of the slurry are removed and placed in 50 ml vials. Each vial thus prepared contains 12.5 grams of XAD-4, 5 grams of C-249 and 3 ml of distilled water.

Vials containing the above resin-water mixture are sterilized by autoclaving at 15 psi for 15 to 20 minutes or are sealed with a vaccine stopper and are sterilized by exposure to cobalt 60 (about 500 to 1000 K rads). The antibiotic removal units which are then ready for use may be used immediately or after a fairly extended storage period.

The above described combination resin permits more rapid determination of the identification and true antibiotic susceptibility of an infecting organism not only when some antibiotics are present in the sample, but also in those cases where a blood sample contains other materials which inhibit the growth of bacteria. When such inhibitory blood is treated with the above described combination non-functional polymeric resin adsorbent and cationic exchange resin, the mixed resin removes the inhibitory substances from the sample. Such substances, however, are removed only by the mixed resin and not by the individual resins.

Where a specimen to be analyzed contains an identified antibiotic, a microporous resin which adsorbs that antibiotic is selected and coated with detergent. However, where a specimen contains one or more unidentified antibiotics, removal thereof may be achieved by selecting a combination of detergent-treated resins which will adsorb various antibiotics. The specimen is contacted with the selected resins in accordance with the above-described methods either serially or simultaneously.

Used resins may be regenerated in accordance with the manufacturers' instructions. Retreatment of the resins with detergents in accordance with the invention is possible thus permitting reuse of the resin materials.

The following examples are illustrative of the invention and are not to be taken in a limiting sense.

EXAMPLE 1

Blood specimens were prepared by adding a particular bacterium to whole blood, which was lysed with an equal volume of distilled water. 10 ml samples of each blood specimen were shaken with 12.5 g of XAD-4 non-ionic polymeric resin adsorbent (Rohm and Haas). In separate 50 ml bottles, a second 10 ml sample of each blood specimen was shaken with 12.5 g of a resin which had been treated with a solution of 0.1% Triton X-100. Residual Triton X-100 had been removed from this resin by aspirating the fluid phase of the resin bed after treatment had proceeded for 15 min. All samples of the blood-water mixture were shaken on a rotary shaker at 250 rpm for 30 min. A control consisting of the blood-water mixture seeded with bacteria and treated with no resin was also employed. The supernatent of each resin treated sample was obtained (eluate), and each eluate and each control was mixed with an equal volume of broth concentrate and then plated (0 hr). The remainder of the sample was incubated at 35° C. for 5 hr and assayed at that time to determine growth rate of the bacteria. The results were as follows:

Table 1.

| Effects of Triton-treated resin XAD-4 on bacteria | | |
|---|---|---|
| | CFU/ml | |
| Bacteria | 0 hr | 5 hr |
| *Staphylococcus aureus* | | |
| Control | 70 | 24,500 |
| Resin eluate (untreated) | 20 | 8,200 |
| Resin eluate (Triton-treated) | 60 | 22,000 |
| *Streptococcus* (group A) | | |
| Control | 190 | 18,000 |
| Resin eluate (untreated) | 40 | 3,200 |
| Resin eluate (Triton-treated) | 60 | 4,500 |
| *Streptococcus* (group D) | | |
| Control | 90 | 20,200 |
| Resin eluate (untreated) | 25 | 5,100 |
| Resin eluate (Triton-treated) | 60 | 11,400 |
| *E. coli* | | |
| Control | 420 | 140,000 |
| Resin eluate (untreated) | 140 | 34,000 |
| Resin eluate (Triton-treated) | 150 | 34,600 |
| *Proteus* | | |
| Control | 55 | 31,900 |
| Resin eluate (untreated) | 10 | 6,000 |
| Resin eluate (Triton-treated) | 45 | 28,300 |
| *Pseudomonas* | | |
| Control | 110 | 41,400 |
| Resin eluate (untreated) | 75 | 33,450 |
| Resin eluate (Triton-treated) | 90 | 37,500 |

As shown in Table 1, in most cases the Triton-treated resin adsorbent reduced the loss of bacteria, as manifested by bacterial counts at 0 hr. When the diluent for the bacteria was urine (5 ml of urine seeded with bacteria), spinal fluid (5 ml of spinal fluid seeded with bacteria), or distilled water (bacteria seeded in water), essentially the same results were obtained. Thus, the adsorption of bacteria to the untreated resin is observed regardless of the diluent and is reduced as exemplified by the results in Table 1, when a resin is pretreated with Triton X-100.

EXAMPLE 2

Using the same procedures as described in Example 1, the sparing effects of various resins treated with Triton X-100 on *Staphylococcus aureus* was determined. The results were as follows:

Table 2

| Resin | Sample | CFU/ml | |
|---|---|---|---|
| | | 0 hr | 5 hr |
| 1-X8 | control | 110 | 37,800 |
| | resin eluate (untreated) | 50 | 10,200 |
| | resin eluate (Triton-treated) | 90 | 36,500 |
| IRA 400 | control | 130 | 39,000 |
| | resin eluate (untreated) | 70 | 31,000 |
| | resin eluate (Triton-treated) | 120 | 38,200 |
| A7 | control | 100 | 36,800 |
| | resin eluate (untreated) | 30 | 7,100 |
| | resin eluate (Triton-treated) | 60 | 15,100 |
| IR45 | control | 125 | 40,000 |
| | resin eluate (untreated) | 20 | 6,200 |
| | resin eluate (Triton-treated) | 70 | 18,900 |
| XAD-4 | control | 120 | 39,400 |
| | resin eluate (untreated) | 30 | 6,800 |
| | resin eluate (Triton-treated) | 105 | 37,400 |

Based on the above results, Triton X-100 treatment appears to result in a bacteria sparing effect regardless of the type of anionic resin used.

A variety of cationic exchanger resins (sodium charged) composed of weak acid acrylic or carboxylic structure, or strong acid polystyrene matrix with quaternary ammonium groups were also tested. The bacterial counts of the control samples and the resin eluates were essentially the same regardless of whether or not the resin was treated with Triton X-100. Thus, cationic resins do not appear to effect the reduction in bacterial count observed with anionic resins.

EXAMPLE 3

Using the methods as described in Example 1, 5 grams of cation resin C-249, 12.5 grams of detergent-treated XAD-4 resin and mixed resins containing 5 grams of C-249 and 12.5 grams of XAD-4 were used. 5 ml of whole blood from volunteers having blood containing inhibitory factors was lysed with 5 ml of water and added to the resins. The results were as follows Table 3

| Bacterial suspension | Diluent | Resin treatment | CFU/ml 0 hr | CFU/ml 5 hr |
| --- | --- | --- | --- | --- |
| E. coli | inhibitory blood | none | 30 | 0 |
|  | non-inhibitory blood | none | 70 | 29,400 |
|  | inhibitory blood | XAD-4 | 25 | 0 |
|  | non-inhibitory blood | XAD-4 | 70 | 30,100 |
|  | inhibitory blood | C-249 | 35 | 0 |
|  | non-inhibitory blood | C-249 | 65 | 28,200 |
|  | inhibitory blood | XAD-4 & C-249 | 70 | 31,000 |
|  | non-inhibitory blood | XAD-4 & C-249 | 65 | 30,100 |
|  | broth only | none | 80 | 32,200 |

As indicated by the results in Table 3, the mixed XAD-4 and C-249 resin treatment effectively removes the inhibitory materials permitting more rapid identification of an infecting organism.

EXAMPLE 4

A mixed resin containing 12.5 grams of XAD-4 adsorbent in which Triton X-100 had been fluidized, 5 grams of C-249 cation resin and 3 ml of distilled water was prepared in a vial. Twenty ml of whole blood was drawn from a volunteer by venipuncture. To the 20 ml of blood was added penicillin G potassium to give a final concentration of 2 ug/ml and 0.1 ml of *Staphylococcus aureus* to produce a final CFU count of about 25/ml. Immediately thereafter, 5 ml of the treated blood was added to a vial of the mixed resin; another 5 ml of treated urine was added to a conventional 50-ml bottle containing blood culture medium.

The resin sample was placed on a rotary shaker for 15 min at 250 rpm, and then 5 ml of the resin eluate was withdrawn and transferred to a duplicate conventional 50-ml bottle containing blood culture medium. Both the resin eluate sample and the control sample which had not been treated with the resin were incubated at 36° C. for 14 days.

At the end of 6 hours the culture inoculated with the resin eluate manifested turbidity, indicating bacterial growth which was confirmed by plating a sample on agar medium. The control blood culture medium sample inoculated with the blood-bacteria-antibiotic mixture failed to manifest any turbidity for the duration of the 14 day incubation period.

EXAMPLE 5

A 20-ml sample of urine was obtained from a volunteer. To the 20 ml of urine was added penicillin G potassium to give a final concentration of 2 ug/ml and 0.1 ml of *Staphylococcus aureus* to produce a final CFU count of about 25/ml. Immediately thereafter, 5 ml of the treated urine was added to a vial containing mixed resin as prepared in Example 4; another 5 ml of treated urine was added to a conventional 50 ml bottle containing culture medium. Both the resin eluate sample and the control sample were incubated at 36° C. for 14 days.

At the end of 6 hours, the culture inoculated with the resin eluate manifested turbidity indicating bacterial growth which was confirmed by plating a sample on agar medium. The control blood culture medium sample inoculated with urine-bacteria-antibiotic mixture failed to manifest any turbidity for the duration of the 14 day incubation period.

EXAMPLE 6

A 20-ml sample of pooled spinal fluid was obtained. To the 20 ml of spinal fluid was added penicillin G potassium to give a final concentration of 2 ug/ml and 0.1 ml of *Staphylococcus aureus* to produce a final CFU count of 25/ml. Immediately thereafter, 5 ml of the treated spinal fluid was added to a vial of mixed resin prepared as in Example 4; another 5 ml of treated spinal fluid was added to a conventional 50-ml bottle containing culture medium. The resin sample was placed on a rotary shaker for 15 min at 250 rpm and then 5 ml of the resin eluate was withdrawn and transferred to a duplicate conventional 50-ml bottle containing culture medium. Both the control and the resin eluate samples were incubated at 36° C. for 14 days.

At the end of 6 hours, the culture inoculated with the resin eluate manifested turbidity indicating bacterial growth which was confirmed by plating a sample on agar medium. The control culture medium sample inoculated with spinal fluid-bacteria-antibiotic mixture failed to manifest any turbidity for the duration of the 14 day incubation period.

EXAMPLE 7

To 20 ml of whole blood, penicillin G and bacteria were added as described in Example 4. Five ml of the blood sample was added to a control blood culture, 5 ml was added to a vial containing only 12.5 grams of XAD-4 adsorbent resin, 5 ml was added to a vial containing only 5 grams of C-249 cation resin, and 5 ml was added to a vial with the mixed resins. After the three resin vials were shaken at 250 rpm for 15 min, 5 ml of the resin eluates were withdrawn from each vial and transferred to blood culture medium as described for the control.

The blood culture control failed to manifest any turbidity after 14 days incubation at 36° C., since the antibiotic was present in the culture. The blood culture inoculated with the eluate from the mixed resin vial manifested turbidity in 6.5 hours. The blood culture inoculated with the eluate from XAD-4 resin also manifested turbidity in 6.5 hours, since this resin is an adsorbent of anionic compounds and penicillin is anionic. The blood culture inoculated with the eluate from the C-249 cation resin failed to manifest turbidity after 14 days incubation, indicating that the cation resin could not remove the drug.

EXAMPLE 8

Using the same procedures as described in Example 7, tests were conducted with blood which contained bacterial inhibitors. The results were as follows:

The control culture was negative for turbidity. The blood culture inoculated with the mixed resin eluate was positive for turbidity in 6.5 hours. The blood culture inoculated with the eluate from the XAD-4 resin was negative for turbidity. The blood culture inoculated with the eluate from the cation resin was negative for turbidity. These results indicate that a mixed resin bed is needed for efficient removal of inhibitor substances present in the blood as well as antibiotics.

EXAMPLE 9

The efficiency of a mixed resin vial made according to Example 4 in removing various antibiotics was treated. The drugs indicated were added to 20 ml of volunteer whole blood obtained by venipuncture to give a final concentration of 2 mg/ml. The blood samples were seeded with the bacteria indicated below to produce a final CFU count of about 25 CFU/ml in each case. In certain cases, the antibiotics used were bacteriostatic against test organisms in order to simulate conditions that often exist in nature, and in other cases bactericidal antibiotics were added. 5 ml of the blood samples were treated with the mixed resin according to the method described in Example 4 and 5 ml were added to a conventional 50 ml bottle containing blood culture medium. After incubating both the resin eluate samples and the control samples for 14 days at 36° C., the following results were obtained:

Table 4

| Antibiotic | Bacteria | Turbidity Control (days) | Mixed resin eluate (hours) |
|---|---|---|---|
| Methicillin (Staphcillin) | Staph. | 3 days | 6 hr |
| Cephalothin (Keflin) | Staph. | none* | 5 hr |
| Carbenicillin (Pyopen) | Staph. | none | 5.5 hr |
| Tetracycline | Staph. | none | 7 hr |
| Ampicillin (Polycillin) | Staph. | none | 9 hr |
| Clindamycin (Cleocin) | Staph. | 5 days | 8 hr |
| Polymyxin B (Aerosporin) | E. coli | 7 days | 5 hr |
| Colistin (Colymycin) | E. coli | none | 6 hr |
| Kanamycin (Kantrex) | E. coli | none | 5.5 hr |
| Erythromycin (Ilotycin) | Staph. | none | 7 hr |
| Neomycin | E. coli | none | 6.5 hr |
| Lincomycin | Staph. | none | 5.25 hr |
| Dihydrostreptomycin sulfate | E. coli | 4 days | 5.75 hr |
| Gentamycin sulfate | Staph. | none | 6 hr |

*None = no turbidity within the 14-day period

These results indicate that treatment of the samples with the mixed resin of the invention resulted in much more rapid detection of bacteria.

What is claimed is:

1. A resin for selectively removing an antibiotic from a bacterially infected body fluid specimen, which comprises a microporous resin coated with a non-ionic detergent, which resin is characterized by the ability to adsorb an antibiotic and is selected from the group consisting of anion exchange resins and non-functional adsorbent resins.

2. The resin of claim 1 wherein the detergent is a polyethylene glycol alkyl aryl ether.

3. The resin of claim 1 wherein the resin is an anionic exchange resin.

4. The resin of claim 1 wherein the resin is a non-functional resin adsorbent.

5. The resin of claim 1 wherein the resin is a non-functional copolymer of styrene and divinyl benzene having a macroreticular structure.

6. The resin of claim 1 wherein the body fluid specimen is blood.

7. The resin of claim 1 wherein the body fluid specimen is urine.

8. The resin of claim 1 wherein the body fluid specimen is spinal fluid.

9. A resin for selectively removing bacterial inhibitors from body fluid specimens, which comprises a microporous non-functional resin adsorbent, coated with a non-ionic detergent, in combination with a cationic exchange resin.

10. The resin of claim 9 wherein the resin adsorbent is a copolymer of styrene and divinyl benzene having a macroreticular structure.

11. The resin of claim 9 wherein the non-ionic detergent is a polyethylene glycol alkyl aryl ether.

* * * * *

UNITED STATES PATENT AND TRADEMARK OFFICE
CERTIFICATE OF CORRECTION

PATENT NO. : 4,145,304
DATED : March 20, 1979
INVENTOR(S) : Joseph L. Melnick and Craig Wallis It is certified that error appears in the above-identified patent and that said Letters Patent are hereby corrected as shown below:

Column 1, line 35, "in such cases in" should read --in such cases is--.

Column 2, line 29, "it" should read --It--; line 47, after "resin" and before "do not" insert the word --and--.

Column 5, line 23, after "However," insert --when--; line 62, delete "placed" and substitute therefor --plated--.

Colume 11, line 5, delete "treated" and substitute therefor --tested--.

Signed and Sealed this

Twelfth Day of June 1979

[SEAL]

Attest:

RUTH C. MASON
Attesting Officer

DONALD W. BANNER
Commissioner of Patents and Trademarks